United States Patent [19]

Hearst et al.

[11] 4,169,204
[45] Sep. 25, 1979

[54] PSORALENS

[75] Inventors: John E. Hearst; Henry Rapoport; Stephen Isaacs, all of Berkeley; Che-Kun J. Shen, Pasadena, all of Calif.

[73] Assignee: Regents of the University of California, Berkeley, Calif.

[21] Appl. No.: 937,292

[22] Filed: Aug. 28, 1978

Related U.S. Application Data

[63] Continuation-in-part of Ser. No. 734,031, Oct. 20, 1976, Pat. No. 4,124,598.

[51] Int. Cl.² ............................................. C07D 403/14
[52] U.S. Cl. ................................... 546/270; 424/246; 424/248.55; 424/263; 424/274; 544/61; 544/150; 546/197; 260/326 R; 260/343.21
[58] Field of Search ...................... 546/270; 260/326 R

[56] References Cited

U.S. PATENT DOCUMENTS

| | | | |
|---|---|---|---|
| 4,124,598 | 11/1978 | Hearst et al. | 260/343.21 |
| 4,129,575 | 12/1978 | Glunz et al. | 260/343.21 |
| 4,130,568 | 12/1978 | Confalone et al. | 260/343.21 |

FOREIGN PATENT DOCUMENTS 859912  4/1978  Belgium ............................. 260/343.21

OTHER PUBLICATIONS

Isaacs et al., Biochemistry vol. 16, pp. 1058 to 1064 (Mar. 22, 1977).

*Primary Examiner*—John D. Randolph
*Attorney, Agent, or Firm*—Jon S. Saxe; George M. Gould

[57] ABSTRACT

New psoralen compounds have been synthesized. The compounds all include the addition of substituent groups at the 4'-position on the basic trioxsalen structure. Specifically, the compounds have the structure

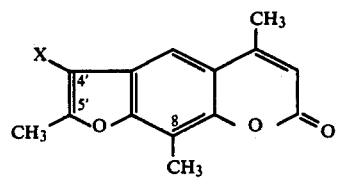

wherein

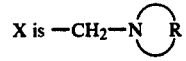

where R is a mono or dicyclic radical which can contain one additional hetero atom in the nitrogen containing ring.

The new substituted psoralens exhibit high solubility in aqueous solution and low dissociation constants from deoxyribonucleic acid (DNA), as well as a reactivity with ribonucleic acids (RNA).

7 Claims, No Drawings

PSORALENS

RELATED APPLICATIONS

This application is a continuation-in-part of copending U.S. Patent Application Ser. No. 734,031 filed Oct. 20, 1976, now U.S. Pat. No. 4,124,598 granted Nov. 7, 1978.

BACKGROUND OF THE INVENTION

Psoralens are the linear isomers of the furocoumarin family and they occur naturally in certain fruits and seeds, e.g., Ammi majus and Psoralea corylifolia. Extracts of these fruits and seeds have been used since ancient times as dermal sensitizing agents in the treatment of vitiligo. Topical application of psoralen extracts, followed by irradiation with light, results in a stimulation of melanin production, thus producing a dermal "tanning" effect.

In recent years, psoralens have been utilized in the photochemotherapy of psoriasis. In such treatment, psoralens are administered orally or topically to a patient. Subsequently, the skin is exposed to ultra-violet radiation. A high percentage of remissions of the disease occur after such treatment.

With increasing study of, and interest in, molecular biology, the psoralens have been investigated with respect to their ability to form covalent bonds with nucleic acids. Because of their planar structure, psoralens can intercalate between the base pairs in the double helix molecular structure of nucleic acids. Upon irradiation with light of the proper wavelength, the psoralens may form covalent bonds with pyrimidine nucleotides that occur as integral entities of nucleic acid strands. Achieving covalently bonded psoralen bridges or crosslinks between the nucleic acid strands of the double helix presents another tool for use in studying, in vivo, secondary structures of nucleic acids. In addition, the psoralens provide a means for inactivating viruses for the purpose of vaccine production, and also as potential chemotherapeutic agents. The covalently bonded psoralens act as inhibitors of DNA replication and thus have the potential to slow down, or stop the replication process. The covalent bond can only be produced in a two step process by first intercalating the psoralen into the nucleic acid helix, and secondly, by exposing those sites to electromagnetic radiation. Thus, it is immediately apparent that the covalent bonding can be controlled both temporally and spacially.

It will be also apparent that crosslinking can only occur for those psoralen molecules that are present at the right place at the right time, i.e., a psoralen molecule must have intercalated in the correct position at the exact moment radiant energy arrives at that site. The presence of a psoralen molecule at the proper position is dependent upon the solubility of the psoralen in aqueous solution and upon the dissociation constant for the non-covalent binding of the psoralen to nucleic acid. Thus, the higher the solubility, the greater number of molecules in the surrounding liquid medium available to binding sites. Similarly, the lower the dissociation constant, the greater the number of psoralens occupying a potential binding site at any moment in time. The dissociation constant, $K_D$, for non-covalent binding of the psoralen to the nucleic acid is defined by the expression:

$$K_D = \frac{(P)(S)}{(PS)}$$

where (P) is the concentration of free psoralen, (S) is the concentration of unoccupied binding sites where each base pair on a nucleic acid is considered to be a binding site, and (PS) is the concentration of psoralen-bound sites.

The subject matter of Ser. No. 734,031, now U.S. Pat. No. 4,124,598, has been published in corresponding Belgian Pat. No. 859,912 (Derwent 30223A/17). Additionally, applicants have published a paper relating to the same subject matter. See Isaacs et al., Biochemistry 16, 1058 (1977). U.S. Pat. No. 3,201,421 teaches the preparation of various mono-, di-, tri- and tetra-alkylpsoralens. U.S. Pat. No. 3,244,729 discloses 5,8-dimethoxy-4-methyl-6,7-furanocoumarins.

BRIEF DESCRIPTION OF THE INVENTION

The present invention is concerned with improved psoralens exhibiting superiority over prior known psoralens with respect to monoaddition to nucleic acids. Superior, in this sense, refers to the resulting density of covalently bound psoralen on the nucleic acid without replenishment of reagent at a common initial concentration of binding sites and total psoralen concentration.

The improved psoralens have two advantages, i.e., they have improved solubilities in water, and/or they have weaker dissociation constants from DNA and/or RNA.

More specifically, it has been found that 4'-substituted psoralens possess the desired properties referred to above.

It is therefore an object of the invention to provide improved psoralens that are 4'-adducts of 4,5',8-trimethyl psoralen (trioxsalen).

It is still another object of the invention to provide psoralens having high solubility in water.

It is yet another object of the invention to provide psoralens having low dissociation constants from DNA and RNA.

It is another object of the invention to provide psoralens having improved abilities to covalently react with DNA and RNA.

Other objects and advantages of the invention will become apparent from the following description and appended claims.

DESCRIPTION OF THE INVENTION

The basic psoralen structure is

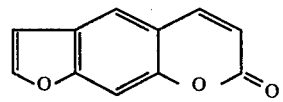

while the two most widely known and widely used derivatives are 8-methoxy psoralen (commonly called methoxsalen):

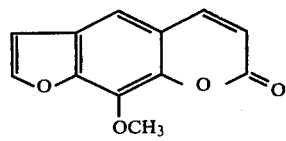

and 4,5',8-trimethyl psoralen (commonly called trioxsalen):

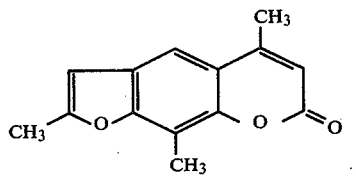

The new psoralens of the invention are all derivatives of trioxsalen in that they are 4'-adducts of trioxsalen. All of the new psoralens have the group

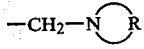

where R is a mono or bicyclic radical which can contain one ring substituent selected from the group consisting of $C_{1-6}$ alkyl and $C_{2-6}$ oxoalkyl and which can contain one additional hetero atom in the nitrogen ring. Suitable hetero atoms include nitrogen, sulfur and oxygen. Examples of R groups including the adjacent nitrogen atom include pyridinyl, piperidinyl, morpholinyl, thiazinyl and phthalimidyl. Examples of ring substituents include methyl, ethyl, n-propyl, 2-oxohexyl and the like. Quaternary salts and pharmaceutically acceptable acid addition salts of the aforesaid compounds are also included within the scope of the present invention.

Preferred embodiments of the compounds of the present invention include: 4'-N-phthalimidomethyl-4,5',8-trimethyl psoralen:

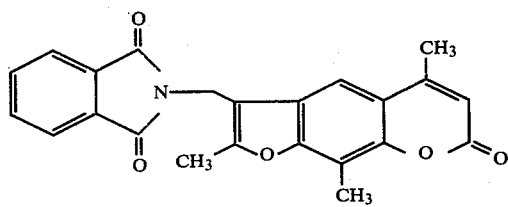

N-(4'-methylene-4,5',8-trimethylpsoralen)pyridinium chloride:

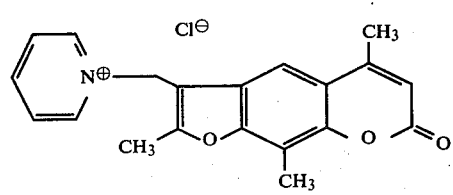

and

N-(4'-methylene-4,5',8-trimethylpsoralen)-3-(butylethanoate)pyridinium chloride

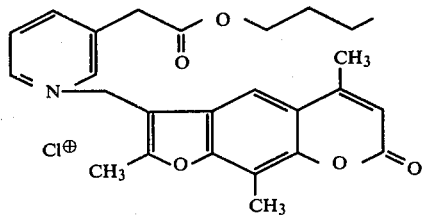

SYNTHESIS OF THE PSORALENS

As a matter of convenience, all the psoralens of the invention can be synthesized from 4,5',8-trimethyl psoralen (trioxsalen) via displacement of the chloro of the corresponding 4'-chloromethyl analog under anhydrous conditions at a temperature in the range of from 0° to 100° C. Trioxsalen is a commerically available psoralen, so it is readily accessible. Although the methods described herein all start with trioxsalen, it will be apparent that other known synthesis methods may be utilized.

For convenience, all syntheses are presented as specific examples, but it should be understood that larger or smaller quantities may be produced in accordance with the methods set foth. Also, variations in the methods set forth will be apparent to those skilled in the art.

EXAMPLE 1

4'-Chloromethyl-4,5',8-trimethyl psoralen

Trioxsalen (659 mg., 2.89 mmole) was dissolved in 75 ml. glacial acetic acid by gentle heating and cooled to room temperature. 5 ml. of chloromethyl-methyl ether was added and the mixture set aside for 24 hours, followed by a second 5 ml. addition of the ether. After 48 hours, the reaction flask was placed on ice and 12 hours later an abundant white precipitate was collected. Another crop was precipitated from the filtrate by addition of 0° water to give 640 mg. total product (yield 80.0%). Analysis of the product produced the following data:

m.p. 215°–17°; NMR (CDCl$_3$) δ2.6–2.7 (9 H, m)4.8(2 H, s)6.3(1 H, s),7.6(1 H, s); mass spectrum m/e (relative intensity) 276 (m+, 48), 278 (m+2,15).

Analysis: Calculated for $C_{15}H_{13}ClO_3$: C, 65.1; H, 4.7; Cl, 12.8. Found: C, 65.0; H, 4.8; Cl, 12.6.

EXAMPLE 2

4'-N-Phthalimidomethyl-4,5',8-trimethyl psoralen

4'-Chloromethyl-4,5',8-trimethyl psoralen (200 mg., 73 mmole) as obtained in Example 1, potassium phthalimide (165 mg., 0.89 mmole, purified by refluxing 2 hours in acetone), and 20 ml. N,N'-dimethylformamide were heated to 100° for 6 hours with constant stirring. The solvent was evaporated in vacuo heating in a water bath leaving behind a yellow paste which was taken up in chloroform and washed three times with water.

The chloroform solution was dried over MgSO$_4$ and then filtered and evaporated to yield 222 mg. (79.3%) of product. Analysis of the product indicated:

m.p. 267°–274°; NMR (CDCl$_3$) δ2.5–2.8 (9 H, m), 5.0 (2 H, s), 6.3 (1 H, s) 7.7–2.8 (7 H, d), 8.0 (1 H, s), mass spectrum m/e (relative intensity) 387 (m+, 80), 241 (20), 240 (75).

EXAMPLE 3

Preparation of N-(4'-methylene-4,5',8-trimethylpsoralen)pyridinium chloride (PMT)

4'-Chloromethyl-4,5',8-trimethylpsoralen (120 mg., 0.43 mm) was placed in 10 ml. dry spectral grade pyridine and stirred at room temperature, dissolving after several minutes to give a yellow solution. After 15-20 minutes a white granular solid had begun to precipitate from solution. Tlc of the mixture (CHCl$_3$/MeOH 98:2) showed the high R$_f$ spot of the starting material plus a non-fluorescent origin spot (product). After 9 hours the amount of precipitate had increased, however, tlc showed starting material was still present. Stirring was continued and tlc re-done at 24 hours, showing a single spot at the origin. The mixture was filtered and the pinkish-white solid sucked dry on the Buchner funnel, followed by vaccum drying (2 hours, 100°, 1 mm) to give 132 mg. (86%) crude product. NMR: (shifts are approximate) d=delta: 1.7, 2.2, 2.7 (9H, 3-singlets, C 4,5',8-methyls), 5.7 (1H, singlet, H3), 6.0 (2H, singlet, C 4'-methylene), 7.2 (1H, singlet, H5), 8.1-9.5 (5H, multiplet, pyridine ring H's). Analysis for crude $C_{20}H_{18}ClNO_3$ (calc/found): C, 67.51/67.18; H, 5.06/5.19; Cl, 9.99/10.03; N, 3.94/4.04. The product was freely soluble in water and was recrystallized from n-propanol/H$_2$O. Additional material in the filtrate was not recovered. UV:

|  | H$_2$O | abs. ETOH |
|---|---|---|
| $\lambda_1(E\lambda_1)$ | 251(25,700) | 243(32,500) |
| $\lambda_2(E\lambda_2)$ | 300(10,500) | 285(12,200) |
| $\lambda_3(E\lambda_3)$ | 330(7,340) | 330(7,670) |

Adducts related to those already specifically disclosed above may be prepared utilizing the same preparation procedures. For purposes of the invention, however, the important properties of such adducts are high solubility in aqueous solution, and a low dissociation constant from DNA and/or RNA.

In order to study solubilities and dissociation constants, it is most convenient to prepare tritiated derivatives of the psoralen compounds. Thus, well-known radiation counting methods may be utilized to monitor the presence of the psoralens in solutions, or in nucleic acids.

The tritium labeled psoralens are prepared from trioxsalen having tritium incorporated therein. Specifically, tritiated water is refluxed with normal trioxsalen to effect an exchange of tritium with the hydrogen on the trioxsalen. The tritated trioxsalen is recovered and utilized to prepare the psoralens of the invention according to the examples previously set forth.

The following example presents a specific method for preparing the tritiated trioxsalen.

EXAMPLE 4

Tritiated 4,5',8-trimethyl psoralen 4,5',8-Trimethylpsoralen (1153 mg.) T$_2$O (aqueous, 100 curies in 4 ml.), dioxane (67.5 ml.) and fuming H$_2$SO$_4$ (30% SO$_3$, 7.5 ml.) were refluxed for 2 hours with constant stirring followed by cooling to room temperature. 125 ml. ice water was added and the mixture cooled on ice for 1 hour. The precipitate was collected by filtration and air dried to give 900 mg. (78%) crude product. Purified trioxsalen (radiochemical purity greater than 99%) was obtained by column chromatography of the crude material. Small samples (20-50 mg) were dissolved in 1-2 ml of chloroform CHCl$_3$, loaded on a 1 cm×30 cm silica gel column (60-200 mesh) and eluted with CHCl$_3$. The fractions containing trioxsalen were combined and the solvent removed. The mass spectrum of the residual white solid found the molecular ion (MW 228) in 100% relative abundance. Analytical TLC of the product (CHCl$_3$/CH$_3$OH 98:2) found more than 99% of the counts in the trimethylpsoralen. The specific activity of the compound was determined by counting aliquots of an absolute ethanol solution of known concentration in toluene-omnifluor. The specific activity was found to be 5×10$^{11}$ dpm/mmole.

Quantities of the psoralens of the invention were prepared as per Examples 1-3 to yield tritiated products which had the same specific activity per mmole as the *chloromethyl trimethyl psoralen from which they were prepared.

The tritiated psoralens were then utilized to study their binding efficiencies with nucleic acid. The studies were directed to securing data on the solubilities and the dissociation constants from both DNA and RNA. In addition, the psoralens' ability to covalently bind with DNA and RNA was also studied.

The studies and results thereof were as follows:

In order to establish the dissociation constants from DNA and RNA, the non-covalent binding was ascertained. Non-covalent binding determines the association of the psoralen within the nucleic acid helix. Its presence is determined in the absence of any radiant energy. As noted before, radiant energy is necessary to activate the psoralen covalent binding reaction with nucleic acid base pairs.

To determine the non-covalent binding, Calf thymus DNA (Sigma Type I) was dissolved in a 0.01 M Tris 0.001 M EDTA pH 7.0 buffer at a concentration of 50 ug/ml. A quantity of this DNA solution was placed in a dialysis bag (pretreated by boiling in NaHCO$_3$), and the various tritiated derivatives were added inside the bag in half the cases and outside the bag in the other half. The molar ratio of psoralen molecules to base pairs was approximately 1:15. The bags were placed in vials filled with 18 ml. of buffer and continually stirred with a magnetic stirrer at 21° C. for 72 hours. After this period, radioactivity was determined both inside and outside the bags and the optical density of the DNA solution measured. From this information, and the specific activity of each derivative, the amount of drug non-covalently bound to the DNA was determined. Binding of the derivatives to Drosophila melanogaster ribosomal RNA was measured in the same manner except that stirring was carried out at 0° C.

The results of the equilibrium dialysis measurements are presented in Table 1 below. The units of the dissociation constants are moles/liter.

Table I

| | DARK BINDING AND PHOTOADDITION TO DNA AND RNA | | | |
|---|---|---|---|---|
| | Dark Binding Constants (a) | | Photoaddition ($\infty$ time) #Psoralens:1,000 Base Pairs (b) | |
| Compound | K$_D$ for DNA | K$_D$ for RNA | DNA | RNA |
| AMT$^{(c)}$ | 6.6 × 10$^{-6}$ | 2 × 10$^{-5}$ | 213 | 196 |

Table I-continued
DARK BINDING AND PHOTOADDITION TO DNA AND RNA

| Com-pound | Dark Binding Constants (a) | | Photoaddition ($\infty$ time) #Psoralens:1,000 Base Pairs (b) | |
|---|---|---|---|---|
| | $K_D$ for DNA | $K_D$ for RNA | DNA | RNA |
| PMT | $2.6 \times 10^{-5}$ | $6.2 \times 10^{-5}$ | 37 | 41 |

(a) Defined as $K_D$ = [Free PMT][Base Pairs]/[Bound Pairs]
(b) Initial Moles Psoralen:Moles Base Pairs = 1:3
(c) 4'-aminomethyl-4,5',8-trimethylpsoralen hydrochloride The covalent binding of the psoralens to DNA and RNA was studied. To achieve covalent binding, it is necessary to supply radiant energy (light) to the binding sites. These studies were carried out as follows:

The DNA and RNA used in the covalent binding studies have been described previously. Samples of each nucleic acid were prepared at a concentration of 25 µg/ml in 0.01 m Tris 0.001 M EDTA buffer. The radioactive-psoralen derivatives were added in a ratio of one psoralen for every three base pairs. The irradiation was carried out in one of the two following devices.

The low intensity irradiations were performed with a modified slide projector which was fitted with a 400 watt General Electric mercury vapor lamp (H 400 A 33-1/T16). The image of the arc was focused on the same cell, jacketed by a cobaltous nitrate solution which was also used for the high intensity irradiations. The light intensity delivered to the sample in this device was 4 to 6 mw/cm². The high intensity irradiations were carried out in a device containing two of the same 400 watt General Electric mercury vapor lamps which were mounted on either side of a double walled sample chamber at a distance between centers of 4.0 cm. The chamber was cooled to 10° C. by continuous circulation of a temperature regulated solution of cobaltous nitrate (40% w/w). The cobalt solution served as an ultraviolet filter which allowed a maximum transmittance of 365 nm light and a window from approximately 340–380 nm. The intensity of the light at the surface of the inner sample chamber was approximately 100 mw/cm². The nucleic acid-psoralen mixture was placed in the inner chamber where it was continuously stirred throughout the irradiation.

A preliminary experiment found the single dose addition rate to plateau after 12 minutes of high intensity irradiation. The PMT/(nucleic acid) solution (1:3 molar ratio in tris/EDTA as above, 1.0 ml. initial volume, 1.0 OD nucleic acid) were irradiated 12 minutes at 320–380 nm (max at 365 nm) at 4° C. After irradiation, the samples were extracted with CHCl₃-isoamyl alcohol (20:1) to remove unreacted PMT and photobreakdown products. After exhaustive dialysis (vs 10 mM tris, 1 mM EDTA; continued until dialysate counts approximate background), the optical density of the nucleic acid solution was measured. Next, the tritium counts associated with the nucleic acid were determined. From this information the amount of PMT covalently bound to DNA or RNA was determined.

Taking samples, at spaced time intervals also permitted an assessment of the kinetics of the covalent binding.

The results are shown under the photoaddition column of Table I.

PMT is an interesting compound for several reasons. First, although PMT is less reactive in both dark and light binding to nucleic acid than AMT, the magnitude of the difference is rather small. In comparison to other psoralen derivatives, PMT is clearly a highly active nucleic acid photoreagent. In addition, PMT is vastly more soluble than any uncharged psoralen thus allowing site saturation of nucleic acid via high concentrations of PMT. It appears that a bulky 4' substituent does not represent a steric barrier to intercalation or photoaddition.

We claim:

1. A compound of the formula

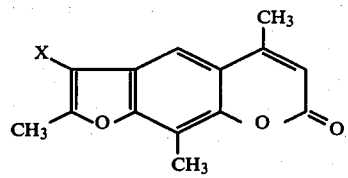

wherein X is

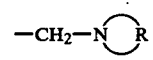

where R is a mono- or bicyclic radical which can contain one ring substituent selected from the group consisting of $C_{1-6}$ alkyl and $C_{2-6}$ oxoalkyl and which can contain one additional hetero atom selected from nitrogen, sulfur and oxygen in the nitrogen ring and quaternary salts and pharmaceutically acceptable acid addition salts thereof.

2. The compound of claim 1 which is 4'-N-phthalimidomethyl-4,5',8-trimethylpsoralen.

3. The compound of claim 1 which is N-(4'-methylene-4,5',8-trimethylpsoralen)-pyridinium chloride.

4. The compound of claim 1 which is N-(4'-methylene-4,5',8-trimethylpsoralen)-3-(butylethanoate)-pyridinium chloride.

5. Tritiated 4'-N-phthalimidomethyl-4,5',8-trimethylpsoralen.

6. Tritiated N-(4'-methylene-4,5',8-trimethylpsoralen)-pyridinium chloride.

7. Tritiated N-(4'-methylene-4,5',8-trimethylpsoralen)-3-(butylethanoate) pyridinium chloride.

* * * * *